(12) United States Patent  
Ikeda (10) Patent No.: US 7,520,979 B2
(45) Date of Patent: Apr. 21, 2009

(54) BLOOD DIALYSIS APPARATUS HAVING CONVENIENT UNIT

(75) Inventor: Atsushi Ikeda, Hiroshima (JP)

(73) Assignee: JMS Co., Ltd., Hiroshima-shi (JP)

( * ) Notice: Subject to any disclaimer, the term of this patent is extended or adjusted under 35 U.S.C. 154(b) by 0 days.

(21) Appl. No.: 11/937,624

(22) Filed: Nov. 9, 2007

(65) Prior Publication Data

US 2008/0105601 A1 May 8, 2008

Related U.S. Application Data

(63) Continuation-in-part of application No. 10/482,293, filed as application No. PCT/JP02/06744 on Jul. 3, 2002, now Pat. No. 7,303,667.

(30) Foreign Application Priority Data

Jul. 3, 2001 (JP) ............................. 2001-202818
Jul. 3, 2002 (JP) ............................. 2002-194447

(51) Int. Cl.
*B01D 61/28* (2006.01)
*B01D 61/32* (2006.01)

(52) U.S. Cl. ........................... 210/143; 210/86; 210/97; 210/321.65; 210/646; 210/744

(58) Field of Classification Search ................. 210/646, 210/739, 744, 86, 87, 143, 321.65
See application file for complete search history.

(56) References Cited

U.S. PATENT DOCUMENTS 7,241,378 B2 * 7/2007 Ikeda ......................... 210/143

7,303,667 B2 * 12/2007 Ikeda ......................... 210/143

FOREIGN PATENT DOCUMENTS

JP 11-221275 A 8/1999
JP 11-226119 A 8/1999

(Continued)

OTHER PUBLICATIONS

English translated Japanese Patent No. 11-221275 filed in parent U.S. Appl. No. 10/484,850.*

(Continued)

*Primary Examiner*—John Kim
(74) *Attorney, Agent, or Firm*—Westerman, Hattori, Daniels & Adrian, LLP.

(57) ABSTRACT

A hemodialysis apparatus which controls dialysis conditions. The hemodialysis treatment is carried out under dialysis conditions determined by defining the course of the chronological target blood indication level as a target control line, measuring the blood indication level at each measurement point (controlling point) in the chronological course, calculating the dialysis conditions using the measured blood indication level and the target blood indication level at the next measurement point (controlling point) of the measurement point in the hemodialysis apparatus carrying out hemodialysis treatment by controlling dialysis conditions using blood volume (BV level) or blood volume change as an indication level (hereinafter blood indication level), to attain the target blood indication level at the next measurement point. This apparatus has a simple control mechanism and has little risk of misoperation or out-of-control. An operator can easily handle it and the control can be quickly and precisely carried out.

5 Claims, 6 Drawing Sheets

FOREIGN PATENT DOCUMENTS

| | | |
|---|---|---|
| JP | 2000-300 A | 1/2000 |
| JP | 2000-140100 A | 5/2000 |
| JP | 2001-540 A | 1/2001 |
| JP | 2002-165876 A | 6/2002 |
| JP | 2002-165877 A | 6/2002 |
| JP | 2002-177226 A | 6/2002 |
| WO | 00/02604 A1 | 1/2000 |

OTHER PUBLICATIONS

International Search Report of PCT/ JP02/06744, date of mailing Oct. 22, 2002.

* cited by examiner

BLOOD DIALYSIS APPARATUS HAVING CONVENIENT UNIT

This application is a continuation-in-part of U.S. application Ser. No. 10/482,293, issued as U.S. Pat. No. 7,303,667, which is a national stage of PCT/JP2002/06744 filed Jul. 3, 2002, which claims priority from Japanese patent application 2001-202818, filed Jul. 3, 2001 and Japanese patent application 2002-194447, filed Jul. 3, 2002. The entire contents of each of the aforementioned applications are incorporated herein by reference.

TECHNICAL FIELD

The present invention relates to a blood treatment apparatus, especially to a hemodialysis apparatus which can control water removal conditions, for example water removal speed so as to prevent excessive water removal and also lack of water removal in the contrary, which occur frequently during hemodialysis.

BACKGROUND ART

For treating patients with impaired kidney function, treatments by purifying blood by dialysis or filtration via semipermeable membrane have been provided conventionally. As for this apparatus, it is important to appropriately maintain the blood volume circulating in the patient body, to perform safe and effective blood purification. A rapid or excessive water removal will decrease excessively patient's blood circulating volume, and it may cause reduction of blood pressure, shock or the like. On the contrary, if the water removal is slow, it will take a long time for blood purification, and if sufficient water removal cannot be made, there is a fear that hypertension, heart failure or the like can occur.

Therefore, a hemodialysis apparatus performing water removal by monitoring patients blood condition have been developed. For example, in Japanese Laid-Open Patent Publication No. 6-83723, an estimating apparatus which estimates the body fluid condition with a Hematocrit meter, and a controlling apparatus which controls the blood pump or ultra pressure by the output of the estimating apparatus are described. Concerning this apparatus, it is convenient as the water removal is controlled directly according to the measured body fluid condition, but on the other hand, as the water removal is controlled directly by the measured value, in case the measuring means is not accurate or a trouble happens, it may cause a significant problem. Therefore, in such feedforward control, generally, a separate line independent from the control line is disposed and a safety mechanism is loaded on the line. However, the apparatus becomes complicated when an independent line or safety mechanism is disposed and the operation becomes difficult. Furthermore, the cost of the apparatus will rise.

Therefore, a simple apparatus as described in Japanese Laid-Open Patent Application No. 9-149935 was also developed. In other words, while monitoring the patient's blood condition, an alarm is ringed depending to the condition, and the water removal pump is stopped. However, this apparatus only recognizes if the water removal control is performed under the same control condition at the time of the initiation of dialysis, by comparing with the blood concentration measured before the initiation of dialysis, and it is not possible to perform adequate water removal to each patent. Furthermore, if the water removal is not performed according to the condition, the operator has to adjust each time the water removal volume or substitutive fluid volume. Thus, even though it was safe, it was complicated and the human cost was high. Moreover, as for the apparatus, a means for measuring the blood condition is disposed on the line at the vein fluid side of the blood cycle, the blood condition after having passed the blood treatment machine (dialyzer) is measured, thus it may not reflect the patient's direct blood condition.

To provide a blood treatment apparatus which have solved the problems mentioned above, that is, to provide a convenient apparatus at a low cost by making a structure wherein each patient's blood condition is monitored, enabling to perform blood treatment adequate to each patient chronologically, by not imposing much burden to the operator during its use, and by making the construction of the blood treatment apparatus simple, the present inventors provided a blood treatment apparatus (Japanese Laid-Open Patent Application No. 11-22175), comprising a blood measuring means for measuring blood parameters; a working unit for performing blood treatment; and a controlling unit controlling the working unit to perform blood treatment under prescribed blood treatment condition, wherein the controlling unit indicates the change of the blood treatment to the working unit, by setting a blood indication region determined beforehand against the patient blood indication level obtained with the blood measuring means, according to the chronological transition of the blood indication level in the blood indication region. Furthermore, the present inventors have improved the blood treatment apparatus (Japanese Laid-Open Patent Application No. 11-22175), and proposed a blood treatment apparatus (Japanese Laid-Open Patent Application No. 2001-540), wherein by monitoring each patient's blood condition, the condition of hemodialysis adequate to each patient chronologically, especially the water removal speed can be easily changed and defined. Said blood treatment apparatus (Japanese Laid-Open Patent Application No. 2001-540) is a hemodialysis apparatus comprising at least: (A) a blood measuring means for measuring blood parameter, (B) a working unit for performing blood treatment; and (C) a controlling unit for controlling the working unit to perform blood treatment under prescribed blood treatment condition; wherein the hemodialysis apparatus has a mechanism for controlling the water removal speed, and the controlling unit (C) incorporates the blood indicating level obtained from the patients' samples by the blood measuring means (A), monitoring if it transits or not within the defined range defined beforehand of blood indication level (hereinafter also referred to as defined range of blood indication level), and when the blood indication level being the target to control deviates from the range defined beforehand, the water removal speed of the working unit (B) can be changed at a speed rate defined beforehand.

As for the hemodialysis apparatus mentioned above, it was possible to manage surely the blood indication level at each point during hemodialysis treatment, but because it was necessary to define the region of the target blood indication level at each point, the operation was complicated. Furthermore, as the defined blood indication level was designated as a range, as long as a blood indication level exists within the defined range (even it is at the absolute edge of the range), the control mechanism of the hemodialysis apparatus would not work. Therefore, in case the blood indication level actually measured is slightly missing the point from the target, there was a fear that the control would be delayed.

DISCLOSURE OF THE INVENTION

The object of the present invention is to provide a hemodialysis apparatus having a controlling unit that controls dialysis conditions, for example the water removal speed, so that the blood volume during hemodialysis can transit appropriately. Moreover, it is to provide a hemodialysis apparatus having improved controlling characteristics wherein the controlling means has a simple mechanism, and is easy to operate, and on the other hand, can carry out controls speedily and precisely.

The present invention provides a hemodialysis apparatus (hereinafter also referred to as first hemodialysis apparatus) that carries out hemodialysis treatment by controlling dialysis conditions, with the use of blood volume (BV level) or blood volume change as an indication level (hereinafter also referred to as blood indication level), wherein the hemodialysis treatment is carried out under dialysis conditions determined by defining the chronological target course of the blood indication level as a target control line, measuring the blood indication level at each measurement point (controlling point) in the chronological course, and calculating the dialysis conditions with the use of the measured blood indication level and the target blood indication level at the next measurement point (controlling point) of the measurement point (controlling point), to attain the target blood indication level at the next measurement point (controlling point). Thus, the object mentioned above was solved.

Figure 3:
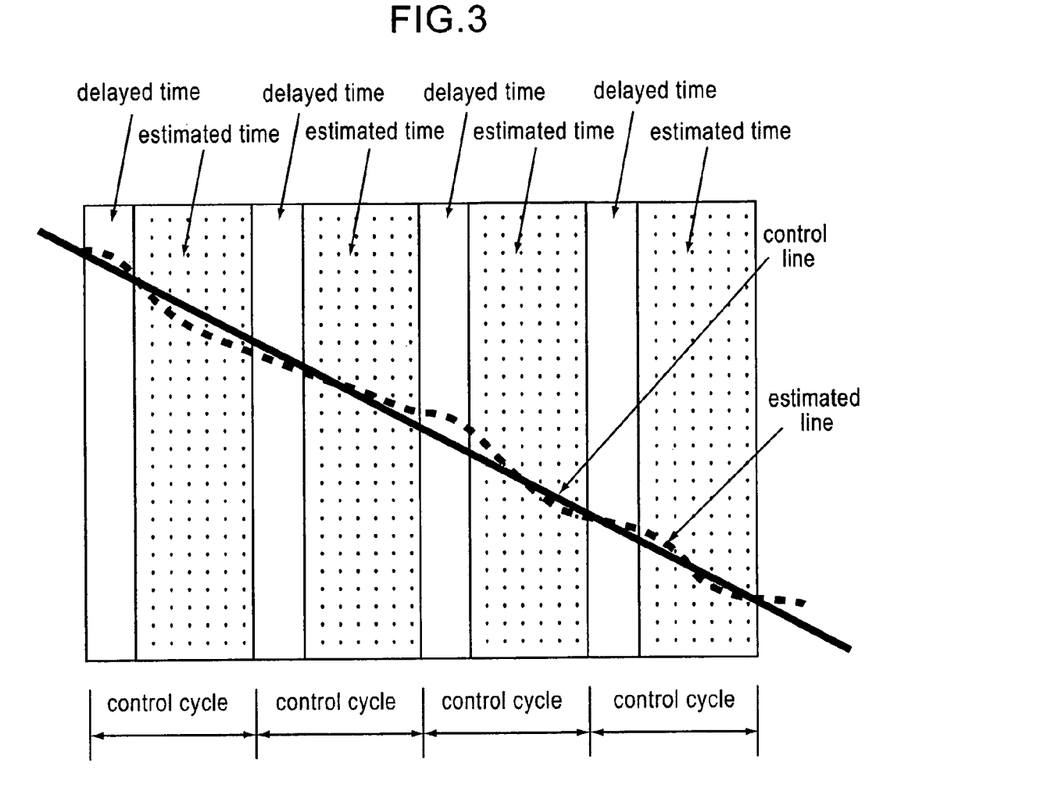
FIG. 3 is a figure explaining that the blood volume change (control delay) appears later than the change of the water removal speed in the hemodialysis apparatus of the present invention.

Furthermore, the present inventors have found that for a hemodialysis apparatus which performs water removal by controlling the blood volume during dialysis according to the target control line as the first hemodialysis apparatus, the blood volume change appears later than the change of the water removal speed, as it is shown in FIG. 3; and that in case the feed-forward control is carried out by disregarding such phenomenon that the blood volume change appears later than the change of water removal speed, as the feed-forward control is a method that uses the blood indication level at the measurement point (controlling point) as the control observed level, it attains the next target blood indication level according to a blood indication level which is different from the blood indication level that is supposed to be attained with the present control level, thus, big changes are observed for the control levels necessary, for example, the control volume necessary to calculate the water removal speed, and therefore, the control would not be stable. The present inventors have solved the problem caused by the control delay by considering the control delay at each control cycle in the feed-forward control.

In other words, the present inventors have improved the feed-forward control by calculating the forecast of dialysis conditions necessary to attain the next target blood indication level (blood volume change), for example the forecast for the water removal speed, according to the blood indication level at the time when the time of control delay have passed.

The improved hemodialysis apparatus is a hemodialysis apparatus (hereinafter also referred to as second hemodialysis apparatus) that carries out hemodialysis treatment by controlling dialysis conditions, with the use of the blood indication level as an indication level, wherein the hemodialysis apparatus is able to carrying out control (feed-forward control) being a hemodialysis treatment carried out under dialysis conditions determined by defining the chronological target course of the blood indication level as a control target line, measuring the blood indication level at the control delay point at each measurement point (controlling point) in the chronological course, and calculating dialysis conditions with the use of the measured blood indication level and the target blood indication level at the next measurement point (controlling point) of the control delay point, to attain the target blood indication level at the next measurement point (controlling point).

Furthermore, the present inventors have provided a hemodialysis apparatus (hereinafter also referred to as third hemodialysis apparatus) that carries out hemodialysis treatment by controlling dialysis conditions, wherein the hemodialysis apparatus is able to carrying out control (feed-forward control) being a hemodialysis treatment carried out under dialysis conditions determined by defining the chronological target course of the blood indication level as a control target-line, calculating the dialysis conditions with the use of each blood indication level at the two adjacent measuring points (controlling points) of the target control line, the water removal speed used between the two measuring points (controlling points), the blood volume at the time of the initiation of dialysis, and the target blood indication level determined by the target control line at the next measuring point (controlling point) of the two measuring points (controlling points) so that the blood indication level attains the target level at the next measuring level (controlling level). Thus, the present inventors have attained the object of the present invention.

The control of the third hemodialysis apparatus (feed-forward control) can be carried out by using the following formula (a).

$$BV_0\{-(\%\Delta BV_{n-1}'-\%\Delta BV_n')+(\%\Delta BV_n'-\%\Delta BV_{n+1}')\}+ UFR_n \times T = UFR_{n+1} \times T \quad (a)$$

(wherein $BV_0$ is the blood volume at the time of the initiation of dialysis; $\%\Delta BV_n'$ is the blood volume change at an optional selected measurement point (n); $\%\Delta BV_{n-1}'$ is the blood volume change at a measurement point (n−1), which is the previous point of the selected measurement point (n); $\%\Delta BV_{n-1}$ is the blood volume change defined at a measurement point (n+1), the next measurement point to carry out feed-forward control; T is the elapsed time until the selected controlling point (n); $UFR_n$ is the water removal speed at the selected controlling point (n); $UFR_{n+1}$ is the water removal speed defined when the control toward the working unit is carried out, to attain the target blood indication level at a controlling point (n+1), the next measurement point of the selected controlling point (n).)

Said formula (a) is obtained as follows:

When each measurement point (controlling point) is set as 1, 2 . . . n−1, n, n+1, relational formulae as follows are obtained.

The first measurement point (controlling point) and the second measurement point (controlling point) are:

$$BV_0[(100\%-\%\Delta BV_1)-(100\%-\%\Delta BV_2)]/T = PRR_1 - UFR_1 \quad (1)$$

$$BV_0(-\%\Delta BV_1'+\%\Delta BV_2')/T = PRR_1 - UFR_1 \quad (2)$$

$$BV_0(-\%\Delta BV_2'+\%\Delta BV_3)/T = PRR_2 - UFR_2 \quad (3)$$

Here, $BV_0$ is BV level, which is the primary blood volume at the time of the initiation of dialysis, $\%\Delta BV_1'$ and $\%\Delta BV_2'$ are the blood volume change at the first or second measurement point (controlling point), T is the elapsed time of dialysis. Moreover, $\%\Delta BV_3$ is the blood volume change determined by the target control line.

Similar relations are obtained at each of any measurement points (controlling point), (n−1) and (n), as it is shown in the following relational formulae.

$$BV_0(-\%\Delta BV_{n-1}'+\%\Delta BV_n')/T = PRR_{n-1} - UFR_{n-1} \quad (4)$$

$$BV_0(-\%\Delta BV_n'+\%\Delta BV_{n+1})/T = PRR_n - UFR_n \quad (5)$$

By subtracting the formula (3) from the formula (2), the following formula (6) is obtained.

$$BV_0\{(\%\Delta BV_1{'}-\%\Delta BV_2{'})-(\%\Delta BV_2{'}-\%\Delta BV_3)\}/T = PRR_1-PRR_2+UFR_2-UFR_1 \quad (6)$$

When it is hypothecated there is no difference between $PRR_1$ and $PRR_2$, that is the distance between the measurement points (controlling point) is defined to be short so as the patient's PPR is not changed substantively at each measurement point (controlling point), the first and second terms in the right side are deleted. Thus, the following formula (7) is obtained.

$$BV_0\{-(\%\Delta BV_1{'}-\%\Delta BV_2{'})+(\%\Delta BV_2{'}-\%\Delta BV_3)\}/T+ UFR_1=UFR_2 \quad (7)$$

In the formula (7), $\%\Delta BV_3$ is the target level at the next measurement point (controlling point), and is a level for the blood indication level to approach by carrying out the control. $UFR_2$ is the water removal speed to define so that the blood indication level of the next measurement point (controlling point) approaches the target level mentioned above. Moreover, $BV_0$ is the BV level at the time of the initiation of dialysis (primary blood volume), $\%\Delta BV_1{'}$ and $\%\Delta BV_2{'}$ are the blood volume change at the first or second measurement point (controlling point), and T is the elapsed time of dialysis.

Said $BV_0$, $\%\Delta BV_1{'}$, $\%\Delta BV_2{'}$ and T are levels already known, and $UFR_1$ is also known as the water removal speed used from the first measurement point to the second measurement point (controlling point). Therefore, if $\%\Delta BV_3$ to be the target is specified, the water removal speed being a dialysis condition can be calculated with the formula (7). The target BV level can be determined by the target control line, from the measurement point (controlling point). On the contrary, if the hemodialysis treatment is carried out with that water removal speed, the BV level at the next measurement point (controlling point) can approach the target level, that is the target control line.

When describing the above formula for any measurement points (controlling points) (n) and (n−1), it is shown as the following formula (8), and as described above, the water removal speed to define so that the blood indication level approaches the target at the next point, according to the blood volume change at the two measuring points (controlling points); the water removal speed between the two measurement points (controlling points); the measurement level for the time of dialysis T; and the blood volume change defined at the next measurement point (controlling point) of the two measurement points (controlling point) determined according to the target control line of the blood indication level.

$$BV_0\{-(\%\Delta BV_{n-1}{'}-\%\Delta BV_n{'})+(\%\Delta BV_n{'}-\%\Delta BV_{n+1})\}+ UFR_n \times T = UFR_{n+1} \times T \quad (8)$$

In the formula (8), $BV_0$ is the blood volume at the time of the initiation of dialysis; $\%\Delta BV_n{'}$ is the blood volume change at an optional selected measurement point (n); $\%\Delta BV_{n-1}{'}$ is the blood volume change at the previous measurement point of an optional selected measurement point; $\%\Delta BV_{n+1}$ is the blood volume change defined at a measurement point to carry out feed-forward control (next measuring point); T is the measured time; $UFR_{n+1}$ is the water removal speed at the selected measurement point; $UFR_{n+1}$ is the water removal speed defined at the next measurement point from the selected measurement point (n), when the control is carried out toward the working unit, to attain the target blood indication level.

However, to obtain the formulae (7) and (8), the condition that "there is no difference between the PRRs at each measurement point (controlling point)", which was hypothecated to derive these formulae, is an assumption, and to meet this condition, it is important that the distance between each measurement point (controlling point) ($\Delta T$) is defined to be short so that there is no difference between the PRRs. Moreover, as for this controlling method, errors to the control may occur due to errors of $BV_0$ at the time of the initiation of dialysis, control delay and other factors, but in the actual control, the control is ensured by defining the water removal speed at each point (measurement point). For example, as it is shown by the graph in FIG. 2, there are substantively no problems for the errors which occur, if the distance between each measurement point (controlling point) is shortened, and the water removal speed is defined each time.

A command of the water removal is taken out at controlling point (n−1) in the 3rd type hemodialysis apparatus. However, the start of actual water removal was the time after controlling point (n−1). This phenomenon is called control delay in this invention. Therefore, it is necessary to adopt $\%\Delta BV_{n-1}{'}$ in consideration of the control delay at the controlling point (n−1) as $\%\Delta BV_{n-1}{'}$ of controlling point (n−1) of the formula (8). As a hemodialysis apparatus in consideration of the control delay, there are the following hemodialysis apparatus, for example.

A hemodialysis apparatus, comprising; a control member, a blood measuring means that measures a blood parameter at the time of hemodialysis passing, converts the blood parameter into a blood index value and conveys to the control member; and an actual working member that performs blood treatment, wherein the control member sets up a target control line which consists of target blood index level determined previously at the time of hemodialysis passing, and calculating a water removal speed which actual working member performs with the use of a blood indication level at a selected controlling point, a blood indication levels in consideration of control delay at a previous selected controlling point adjacent to the selected controlling point, a water removal speed used between the selected controlling point and the previous controlling point adjacent to the controlling point, a blood volume at the time of the initiation of hemodialysis and a target blood indication level determined by the target control line at the next controlling point of the selected controlling point.

In the 3rd type hemodialysis apparatus, the control member can control the water removal speed of the actual working member for example, based on the following formula (9).

$$BV_0\{-(\%\Delta BV_{n-1}{'}-\%\Delta BV_n{'})+(\%\Delta BV_n{'}-\%\Delta BV_{n+1})\}+ UFR_n \times T = UFR_{n+1} \times T \quad (9)$$

wherein $BV_0$ is the blood volume at the time of the initiation of hemodialysis; $\%\Delta BV_n{'}$ is a ratio of the blood volume change at the selected controlling point (n); $\%\Delta BV_{n-1}{'}$ is a ratio of the blood volume change in consideration of control delay at a previous controlling point (n−1) adjacent to the controlling point (n) by the target control line; T is the elapsed time until the selected controlling point (n); $UFR_n$ is the water removal speed at a selected controlling point (n); $UFR_{n+1}$ is a calculated water removal speed when the actual working unit is carried out the water removal from the selected controlling point (n) to the controlling point (n+1), to attain the target the ratio of the blood volume change defined at a next controlling point (n+1). $\%\Delta BV_{n-1}{'}$ of the aforementioned formula (9) is $\%\Delta BV_{n-1}{'}$ in consideration of control delay in the aforementioned formula (8). And $\%\Delta BV_{n-1}{'}$ of the consideration of control delay of the aforementioned (9) formula can be determined, for example, with the alignment least square method, as follows.

Figure 8:
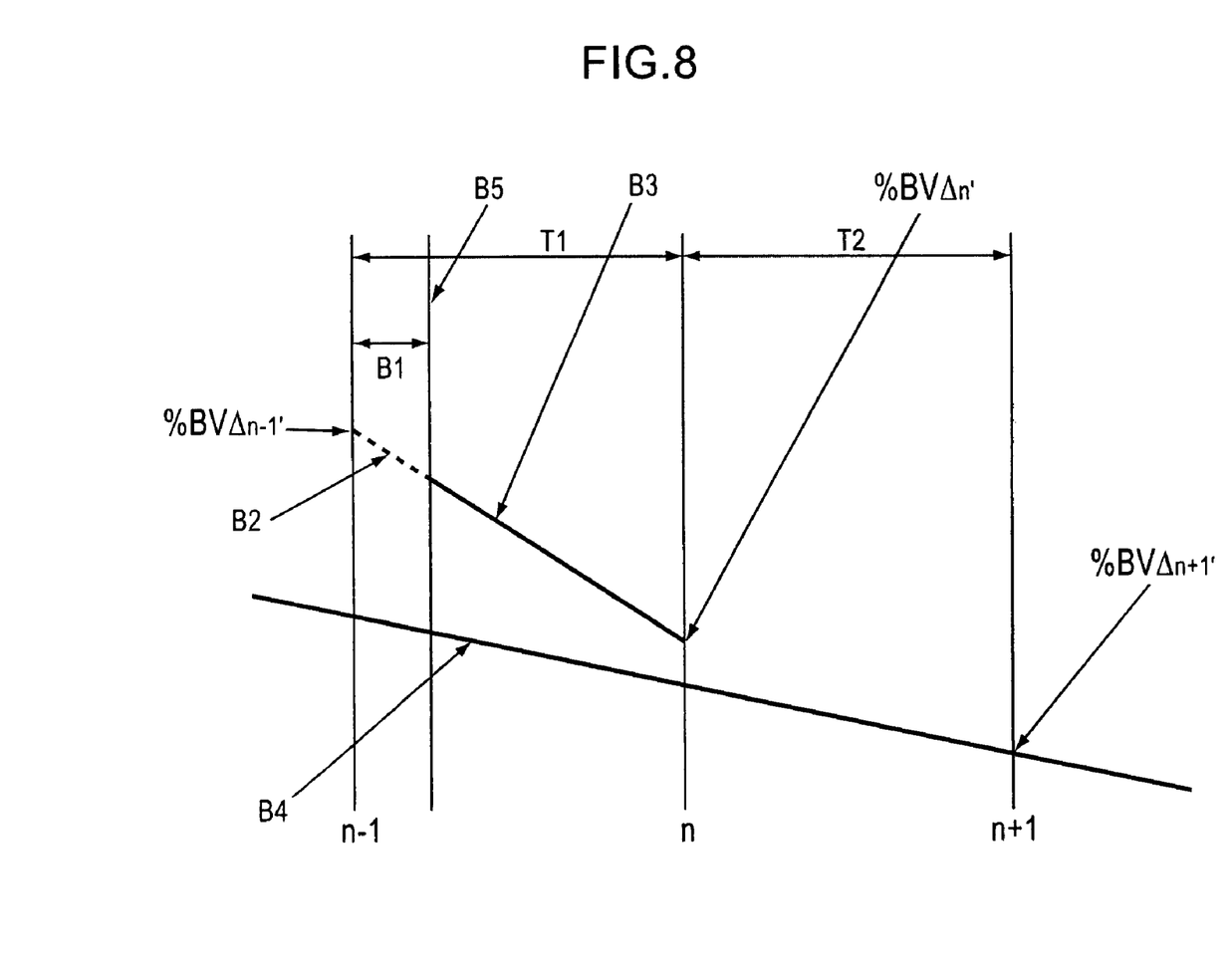
FIG. 8 is a figure explaining the determination of %$\Delta BV_{n-1}$' of the consideration of control delay of the aforementioned formula (9) with the alignment least square method.

It is explained referring to FIG. 8. Based on the alignment least square method, straight line B3 is computed from two or more data sampled between control cycles T1 except a control delay period. Straight line B2 is computed by extending the straight line B3 toward the controlling point (n−1) side by the same inclination. The %ΔBV$_{n-1}$' in consideration of control delay at the controlling point (n−1) is the %ΔBV$_{n-1}$' at the controlling point of the straight line B-2. The vertical axis of this FIG. 8 is %ΔBV, and a horizontal axis is the lapsed time of hemodialysis passing. The method of the common use adopted as arrangement of measurement data can be used for the alignment least square method adopted by this invention. The control delay period can set up arbitrary time between controlling point n and controlling point n−1.

B1: control delay period.
B2: the straight line which extended straight line B3 toward the controlling point n−1 side by the same inclination.
B3: the straight line computed based on alignment least square method from two or more %ΔBV data sampled between control cycles T1 except a control delay period.
B4: the target control line
B5: the control delay line
n: the selected controlling point
n−1: the controlling point before adjoining controlling point (n)
n+1: the controlling point after adjoining controlling point (n)
%ΔBV$_n$': a ratio of the blood volume change at selected controlling point (n)
%ΔBV$_{n-1}$': a ratio of the blood volume change in consideration of control delay at controlling point (n−1)
%ΔBV$_{n+1}$: the target ratio of the blood volume change defined at controlling point (n+1) by the target control line B4.
T1: control cycle
T2: control cycle In the meantime, a control carried out by using a target control line such as that described above, with the use of the blood indication level at each measuring point the next target blood indication level of the each measurement point, or calculated dialysis conditions as parameters, is also called a feed-forward control.

Figure 1:
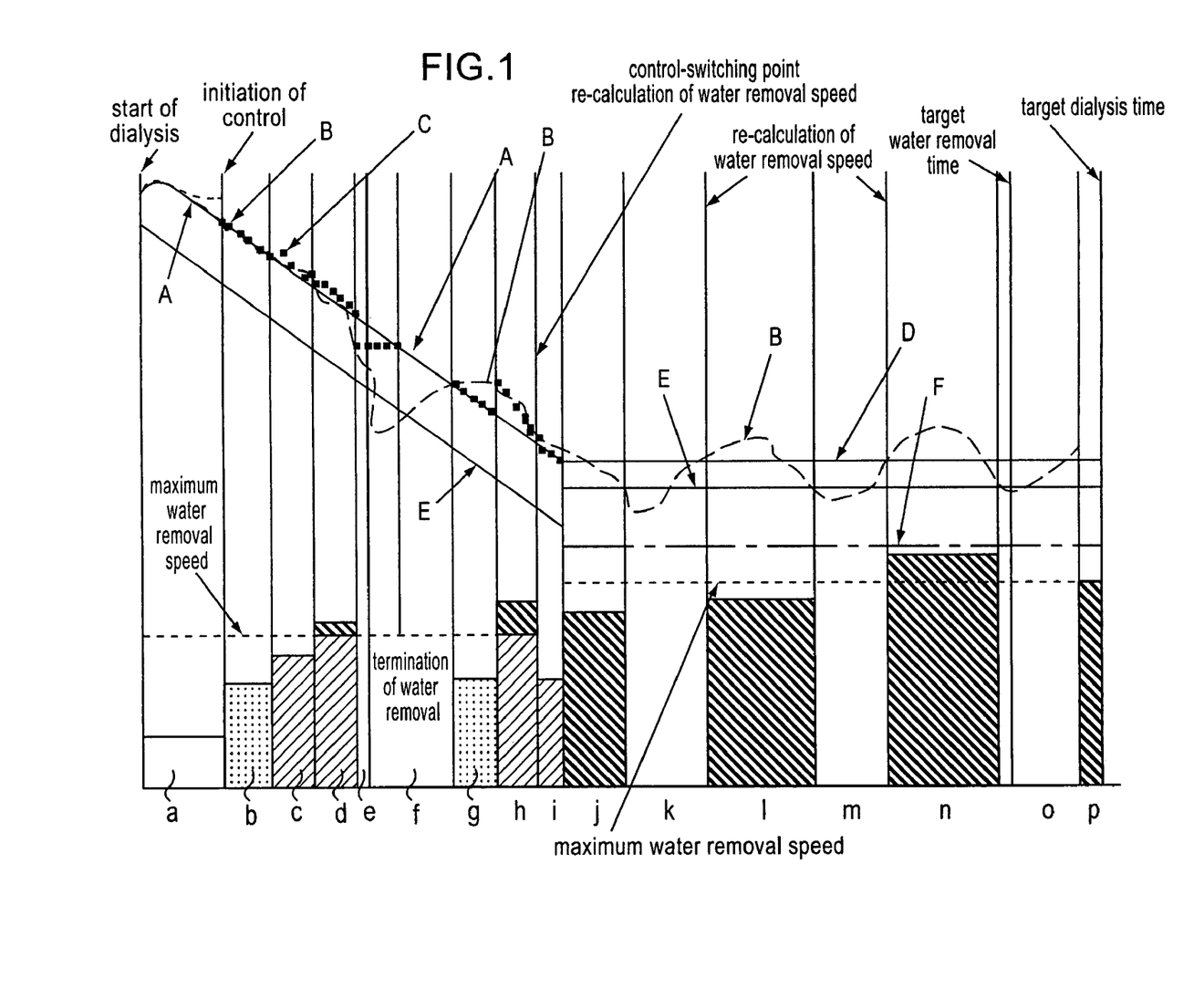
FIG. 1 is a figure explaining the embodiment of dialysis conditions (water removal speed) according to the estimated control line of the hemodialysis apparatus of the present invention.

Furthermore, the present inventors have found that the control delay appears significantly at a point wherein the target control line changes drastically, for example, at a point in the vicinity of the limit of the former part of dialysis operation, performing dialysis operation which decreases the blood volume according to the target control line A as shown in FIG. 1, and the latter part of dialysis operation, performing dialysis operation to maintain the blood volume substantively stable, and that it is possible to solve the problems by the adapting means as follows, which occur when the control delay appears significantly.

Figure 4:
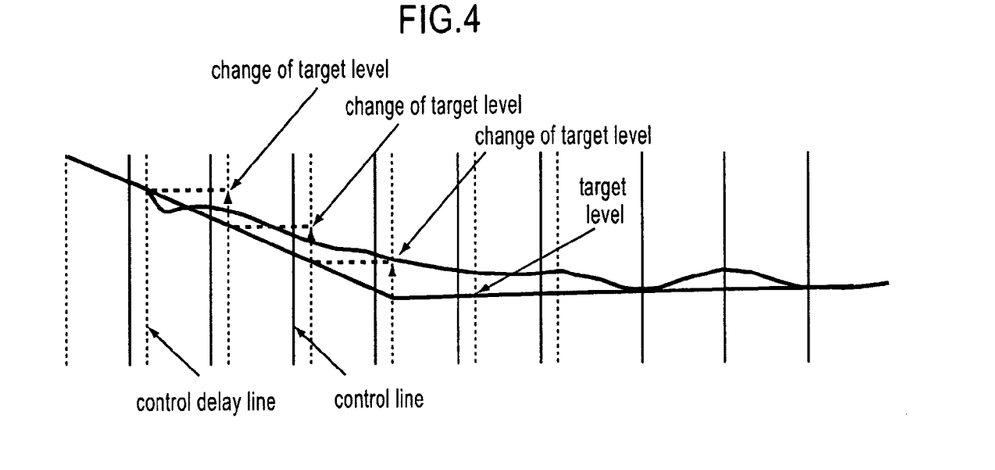
FIG. 4 explains that to solve the problem of the control delay occurring significantly just before the vicinity of the former control part and the latter control part during control using the hemodialysis apparatus of the present invention, the control is carried out by changing in advance the next target blood indication level at multiple measurement points (controlling points) of control cycle defined beforehand just before the limit between the former control and latter control, to approach the condition of the target definition line of the latter part for the each control cycle.

In other words, as for a method to solve the problems, a method of changing beforehand the next target at multiple control cycles, just before the limit between the former control and the latter control, so that it approaches to the condition of the target defined line of the latter part (in the present figure, it is in a horizontal condition), at each the control cycle. Concretely, it can be exemplified as it is shown in FIG. 4, by a method of moving horizontally the target level for one cycle respectively at each measurement point (controlling point) described above, to moderate the drastic change between the former part and the latter part. In the meantime, the number of control cycles which was defined beforehand, can be of any value, as long as it is within the range that the object of the present invention can be solved.

Figure 5:
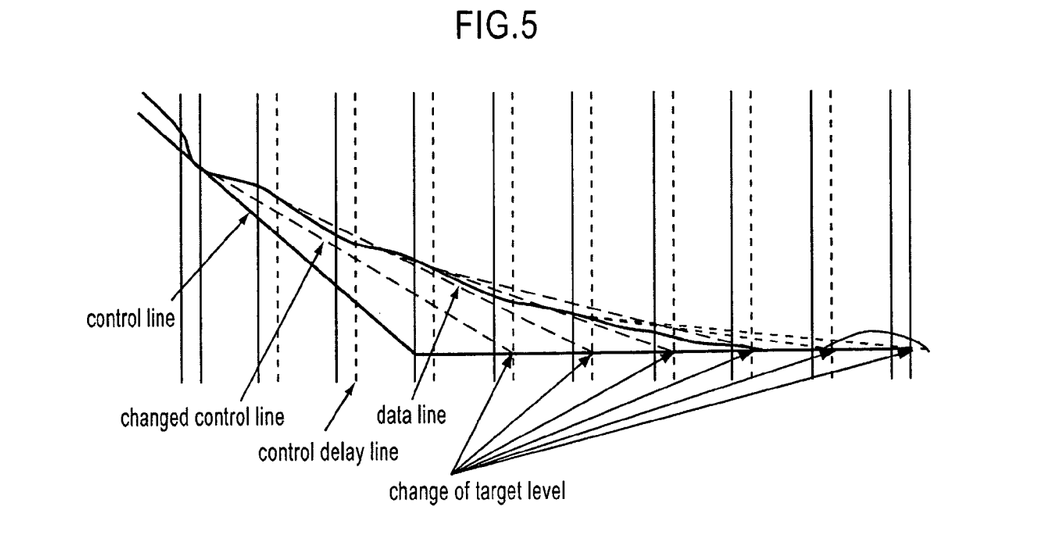
FIG. 5 explains that to solve the problem of the control delay occurring significantly just before the limit between the former control part and the latter control part during control, the control line is changed so that the change of the target control line in the vicinity of the limit between the former part and the latter part of dialysis is small, and the control for the multiple control cycles in the vicinity of the limit between the former part and the latter part of dialysis, is carried out according to the changed control line.

Moreover, as for the problem of the control delay, it was also solved, for example, by changing the control line that reduces the drastic change of the target control line in the vicinity of the limit between the former part and the latter part of dialysis, that is, by changing the control line that moderates the inclination of the target control line, and by carrying out the control according to the target control line that have been changed. Concretely, as shown in FIG. 5, an example of carrying out the control by shifting the next target point of the multiple control cycles, in the vicinity of the limit between the former part and the latter part of dialysis, to a more latter part of dialysis, can be exemplified.

In the following, examples and methods for calculating the blood volume to be used as blood indication level or the blood volume change and primary blood volume for the hemodialysis apparatus of the present invention will be explained.

1. Blood Volume (BV) and Blood Volume Change which are Possible for Use (1) BV Level There is no specific limitation for the blood volume that can be used in the present invention, as long as it shows a blood volume that circulates in the patients' body, and Hematocrit level (also referred to as Ht, abbreviated) can be exemplified.

(2) ΔBV Level

It refers to the change volume of the blood volume, and is the change volume of the blood volume per time unit. It can be calculated from Ht, according to the following formula.

$$\Delta BV [BV \text{ change volume}] = (Ht \text{ at the time of the initiation of dialysis}/Ht \text{ at the time of measurement}) - 1$$

(3) %ΔBV

It is the ratio of the blood volume change, and is shown by the following formula.

$$\%\Delta BV = \Delta BV (\Delta BV \text{ level at the time of measurement})/BV_0 (BV \text{ level at the time of the initiation of dialysis}) \times 100$$

(4) BV %

It is calculated by dividing the BV level at the time of measurement by $BV_0$ which is the BV level at the time of the initiation of dialysis (also referred to as primary blood volume) and is expressed in percentage. It is shown by the following formula.

$$BV\% = BV \text{ level at the time of measurement}/BV_0 \text{ which is } BV \text{ level at the time of the initiation of dialysis (primary blood volume)} \times 100$$

2. Definition of Other Parameters and Formulae for Calculating (1) Definition of PRR PRR is an abbreviation for Plasma Refilling Rate, and is defined as speed of the blood plasma refilling from the body to the blood vessel, and shows the patient's water removal ability at each point.

(2) Formula for Calculating PRR

PPR is calculated with the following formula:

$$PRR_n - UFR_n = \Delta BV_n'/T_n$$

(wherein PRR$_n$ is the Plasma Refilling Rate at an optional selected measurement point (n), UFR$_n$ is the water removal speed at an optional selected measurement point (n), ΔBV$_n$' is the blood volume change at an optional selected measurement point (n), T$_n$ is the elapsed time until an optional selected measurement point (n)).

Said blood volume at the time of the initiation of dialysis (primary blood volume) $BV_0$ which is the control parameter for the hemodialysis apparatus of the present invention, is the sum of the circulating volume in the body and the circulating volume outside the body, and can be calculated by the following methods for calculating (1) or (2).

(1) Method for Calculating (1)

Figure 6:
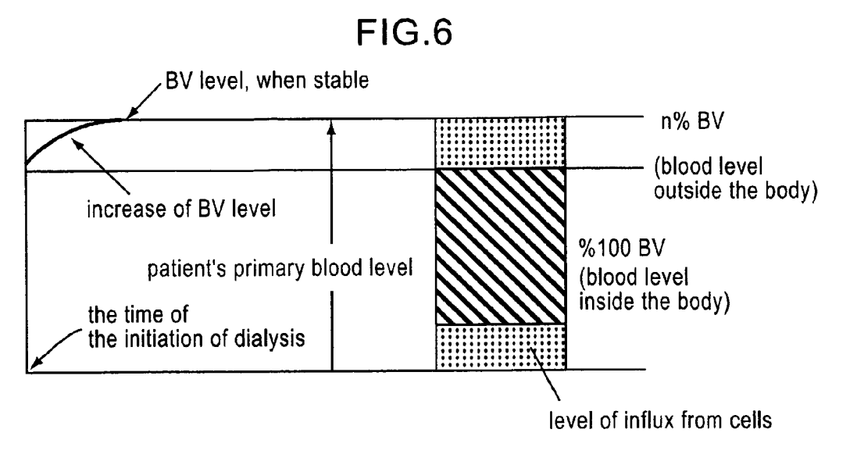
FIGS. 6 and 7 are figures explaining the method for calculating the primary blood volume.

The first method for calculating the primary blood volume ($BV_0$) is explained according to FIG. 6.

At the time of the initiation of dialysis, as the blood volume is not stable, the water removal is not performed, and only the circulation outside the body is performed. By continuing the circulation outside the body until the blood volume stabilizes, in case the turgor pressure inside the cells is sufficiently high, and the water run over the cells and is accumulated up to the cell stroma, it is believed that the body fluid (the inflow volume from the cells of FIG. 6) corresponding to the increased blood volume circulating outside the body (space outside the body) will move from the cells to the blood vessel. Therefore, it is possible to obtain the primary blood volume ($BV_0$) for each patient, according to the following formula with the increased blood volume circulating outside the body (space outside the body) and %ΔBV.

Primary blood volume($BV_0$)=increased blood volume circulating outside the body (space outside the body)/%ΔBV.

(2) Method for Calculating (2)

Figure 7:
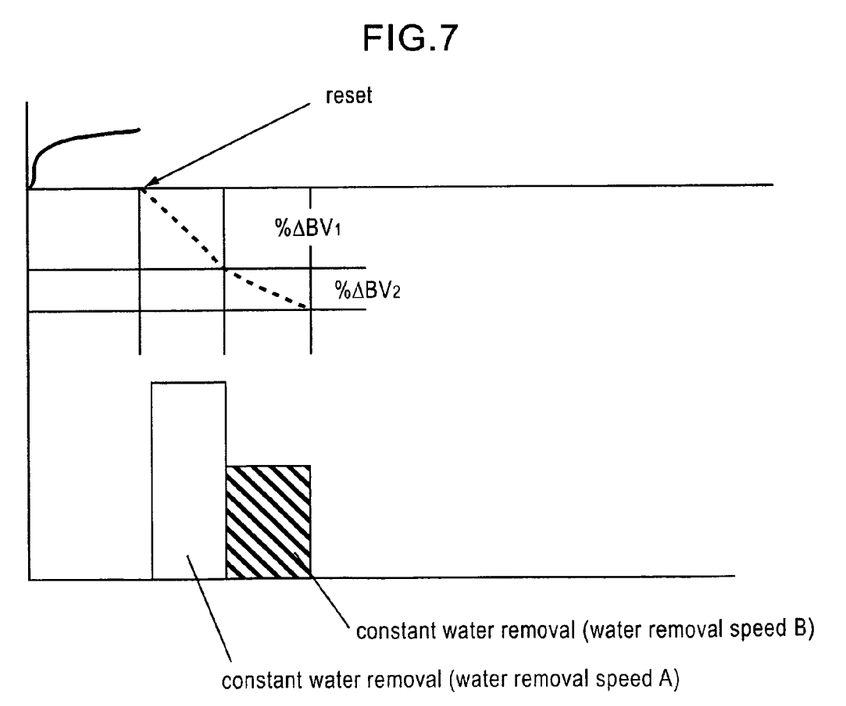

The first method for calculating the primary blood volume ($BV_0$) is explained according to FIG. 7.

By using the hemodialysis apparatus which controls dialysis conditions according to the blood indication level, only the circulation outside the body is performed at the time of the initiation of dialysis as shown in FIG. 7, the circulation outside the body is continued until BV level stabilizes, and when the BV level becomes stable, dialysis accompanied by water removal is initiated, and at the same time as the dialysis is initiated, the water removal is performed with a certain time ΔT (within the time PRR does not change), and with a certain water removal speed (water removal speed A), and thus $ΔBV_1$, which is the change volume of the BV level is calculated. Then, the water removal is performed for the same time as the certain time ΔT with a different water removal speed (water removal speed B), and thus, $ΔBV_2$ which is the change volume of the BV level, is calculated. Thus, $BV_0$ can be calculated by using the $ΔBV_1$, the $ΔBV_2$, water removal speed A and water removal B.

The primary blood volume ($BV_0$) of each patient calculated by the method, can be calculated concretely according to the following formula.

$$BV_0=(\text{water removal speed } A-\text{water removal speed } B)/(-ΔBV_1\%+ΔBV_2\%)\times ΔT$$

Said formula can be calculated as follows:

$$ΔBV/ΔT=PRR-UFR$$

$$-ΔBV_1/ΔT+ΔBV_2/ΔT=\text{water removal speed } A-\text{water removal speed } B$$

$$ΔBV_1=ΔBV_0[(100\%-\%ΔBV_1)-(100\%-\%ΔBV_1')]$$

$$ΔBV_2=ΔBV_0\times\%ΔBV_2$$

$$BV_0/ΔT(-\%ΔBV_1+\%ΔBV_2)=\text{water removal speed } A-\text{water removal speed } B$$

$$BV_0/ΔT=(\text{water removal speed } A-\text{water removal speed } B)/(-\%ΔBV_1+\%ΔBV_2)$$

When the $BV_0$ which is the primary blood volume is obtained as mentioned above, it is preferable to calculate automatically the target BV % by using the $BV_0$ level which is the blood volume inherent to each patient and the standard blood volume (BVst) which is defined beforehand by doctors and the like, according to the following formula (c), and to carry out control with the use of the target BV % as the control object level of the hemodialysis apparatus of the present invention. In the meantime, the standard blood volume (BVst) is the blood volume within the range that a healthy person maintains, and it is preferable to control the hemodialysis apparatus of the present invention to approach to the range of this blood volume.

$$\text{Target } BV\%=\text{standard blood volume}(BV_{st})/\text{primary blood volume}(BV_0)\times 100$$

Said standard blood volume ($BV_{st}$) is a level of the blood volume ($BV_{st}$) which the patient would have if healthy, defined beforehand by doctors and the like by considering factors that might influence the human blood volume, for example the patient's age, sex, body height and the like.

Hereinafter, the control line used to control the hemodialysis apparatus of the present invention will be explained.

Figure 2:
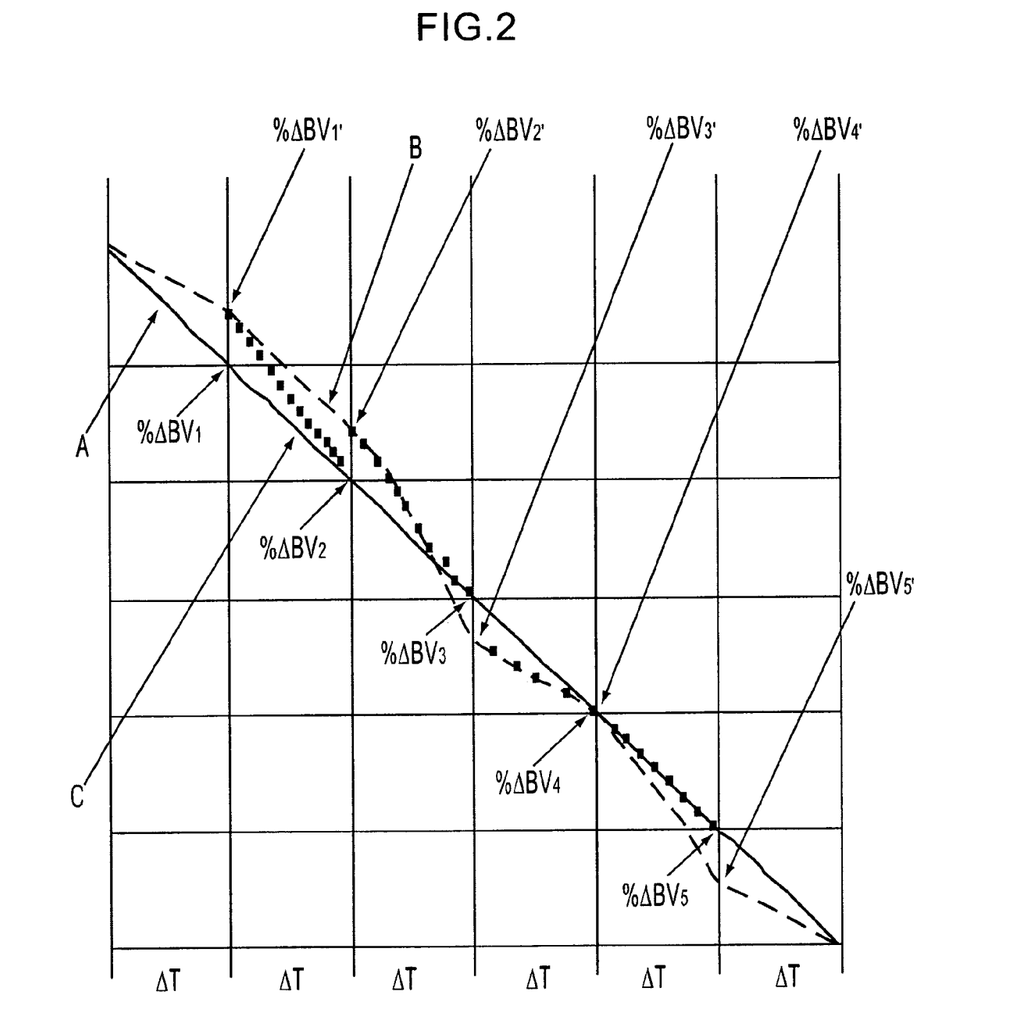
FIG. 2 is a figure showing the relationship of the target control line A, data line B and estimated control line C, during the former part of the water removal operation using the hemodialysis apparatus of the present invention.

(1) Target Control Line:

It will be explained according to FIGS. 1 and 2.

In FIG. 1, it is shown by a hatched line A in the former part of dialysis, and by a horizontal line D in the latter part of dialysis. According to this target control line A of FIG. 1, in the former part of dialysis, a dialysis operation, for example water removal, which decreases the blood volume reasonably to the body is performed, and in the latter part of dialysis operation, a dialysis operation, for example water removal, which maintains the blood volume suitable to each patient according to the target control line D, that is, to maintain the blood volume substantively constant is performed. Moreover, it is shown by a hatched line A of FIG. 2. The vertical axes of FIGS. 1 and 2 show the blood indication level, for example, %ΔBV level in FIG. 2, and the horizontal axes show the elapsed time from the initiation of dialysis. Therefore, this target control line is an indication of the chronological course or the target level of the blood indication level, and the target control line is defined before dialysis by doctors and the like.

(2) Estimated Control Line

It will be explained according to FIGS. 1 and 2.

By using the blood indication level according to the measurement levels such as BV, ΔBV or %ΔBV and the like at the measuring point (controlling point) and the target blood indication level shown by the target control line A at the next measurement point (controlling point), the dialysis conditions (for example, the water removal speed) to attain the target blood indication level at the next measurement point (controlling point) is calculated, and the hemodialysis treatment is carried out under this calculated dialysis conditions (for example, the water removal speed), to attain the next measurement point (controlling point). As a result, the data line B which will likely slip away from the target control line A, will be corrected by the dialysis conditions newly defined at every measurement point (controlling point), and therefore become the estimated control line C, which transits along the target control line A.

(3) Deviated Control Line

The hatched line downward sloping showed beneath the target control line A of FIG. 1 is the alarm line to function as a deviated control line E. In case dialysis operation is carried out under the control of the hemodialysis apparatus of the present invention, the feed-forward control will function, but in case the blood indication level exceeds the deviated control line E, it is preferable to adapt an emergency control different from the standard control method. For example, as it is shown in the graph in FIG. 1, in case the data line B showing the transition of the data level deviates beneath the alarm line E, the water removal means such as water removal pump and the like should be stopped, or if necessary, a substitutive fluid to the patient using a substitutive fluid pump is performed by priority before carrying by the control by feed-forward. Thus, the hemodialysis apparatus of the present invention does not only have the function to approach the blood indication level to the target, but in case the blood indication level is deviated in a dangerous region, it is possible to ensure the safety of the patient by preferentially operating the emergency control. The defined water removal speed is shown in the bottom half of the graph in FIG. 1.

BRIEF DESCRIPTION OF DRAWINGS

Moreover, in each figures mentioned above, A is the target control line; B is the data line; C is the estimated control line; D is the target control line; E is the alarm line; F is the urgent liquid supply line; a, b, c, d, e, f, g, h, i, j, k, l, m, n, o and p are water removal speed; %$\Delta BV$ is the blood volume change measured at each measurement point (controlling point); and $\Delta T$ is the measured cycle (control cycle), respectively.

BEST MODE OF CARRYING OUT THE INVENTION

In the following, embodiments of control for dialysis operation of the present invention will be explained according to FIG. 1. In the bottom half of FIG. 1, the defined water removal speed is shown.

1. Former Part of Dialysis (1) Start of Dialysis

When starting dialysis, as the BV level is unstable, the water removal is not performed at the time of the initiation of dialysis (water removal speed a=0), only the circulation outside the body is performed, and it is waited for the time interval to pass until the BV level stabilizes.

(2) The Time of the Initiation of the Measurement

After the BV value is stabilized, the hemodialysis apparatus is reset and the water removal is started. Just after the initiation of water removal (first control cycle), as previous control cycle does not exist, and the water removal speed is impossible to predict, the water removal is started without carrying out the control. As for the water removal, BV.sub.0 level inherent to this patient is obtained from the weight before dialysis, and according to the $BV_0$ level (primary blood volume), the water removal speed (b) is calculated to attain the target control line at the next controlling point, and the hemodialysis is carried out with the water removal speed. Then, the feed-forward control is initiated and the water removal is performed with the water removal speed ((c) to (e)).

In case the water removal speed determined as above mentioned, exceeds the maximum water removal speed prescribed beforehand, the hemodialysis is carried out with the maximum water removal speed. For example, among the water removal speed (a) to (i) shown in FIG. 1, the water removal speed (d) and (h) exceed the maximum water removal speed line (the black part of the water removal speed in the figure), therefore the maximum water removal speed is used as the water removal speed. In the meantime, when the water removal speed exceeds the maximum water removal speed, it is most preferable to use the maximum water removal speed as the water removal speed, but it may be a water removal speed less than the maximum water removal speed. Moreover, as the observed level of the blood indication level during dialysis at water removal speed (f), becomes less than that of the alarm line, the water removal speed f=0 (that is, water removal is not performed).

As a result of the termination of the water removal, the water removal is started again when the blood indication level exceeds the control line. The primary water removal speed of control when the water removal is started again, is determined with the same method as for the water removal speed (b) mentioned above, and the water removal is performed. When the water removal volume predetermined for the former part of dialysis has been removed, the control of water removal for the latter part of dialysis is started.

2. Latter Part of Dialysis

The water removal speed is calculated to finish removing the remaining water removal volume within the target water removal time, and the water removal is performed with the water removal speed. When performing water removal with this water removal speed, the water removal is stopped in case the blood indication level becomes less than the alarm level. For example, when the water removal is performed with the water removal speed (j), the blood indication level, for example, the blood volume change; became less than the alarm level. Therefore, the water removal at the next controlling point is stopped, and the water removal speed (k) was set to 0. Moreover, as the water removal was stopped, the actual blood volume change $\Delta BV$ level have been recovered to be above the alarm level, the water removal speed is calculated so that the remaining water removal volume at that control time is finished to be removed within the target water removal time (determined water removal volume), and the water removal is performed with the determined water removal speed (l). By performing the water removal with the determined water removal speed (l), the actual $\Delta BV$ level becomes less than the alarm level again. Therefore, the water removal at the next controlling point is stopped and the water removal speed (m) was set to 0.

Furthermore, as a result of termination of the water removal, as the actual $\Delta BV$ level have been recovered to be above the control line, the water removal speed is calculated so that the remaining water removal volume at that control time will finish to be removed within the target water removal time (determined water removal volume), and the water removal is performed with the determined water removal speed (n). However, as the water removal speed (n) of the determined water removal speed exceeds the maximum water removal speed, the maximum water removal speed was used as the actual water removal speed. As the target water removal volume was not finished removing by the end of the target water removal time, the water removal was performed with the maximum water removal speed up to the target removal volume, and the dialysis was finished.

In the meantime, as for dialysis operation of FIG. 1, the former part of the control is carried out by the feed-forward control, but according to the hemodialysis apparatus of the present invention, the feed-forward control may also used for the entire control period of dialysis operation.

INDUSTRIAL APPLICABILITY

According to the present invention, a hemodialysis apparatus having excellent effects as follows can be obtained.

(1) The control mechanism is simple, and there is little risk of misoperation or out-of-control.

(2) As there is no need of difficult installation or unnecessary operation, the operator can easily operate without difficulty.

(3) As the control is carried out rapidly and finely, the blood volume can be transited fairly during the hemodialysis.

(4) By carrying out a control by considering the control delay, the control of dialysis conditions can be carried out more exactly.

What is claimed is:

1. A hemodialysis apparatus, comprising;
a control member,
a blood measuring means that measures a blood parameter at the time of hemodialysis passing, converts the blood parameter into a blood index value and conveys the blood index value to the control member; and
an actual working member that performs blood treatment, wherein the control member sets up a target control line which consists of a previously determined target blood index level, and
wherein the control member controls a water removal speed by feed forward control based on a blood indication level at a selected controlling point, blood indication levels which are in consideration of a control delay at a previous selected controlling point adjacent to the selected controlling point, a water removal speed used between the selected controlling point and the previous controlling point adjacent to said controlling point, a blood volume at the time of the initiation of hemodialysis, and a target blood indication level determined by said target control line at the next controlling point after the selected controlling point.

2. The dialysis apparatus according to claim 1, the control member controls water removal speed $UFR_{n+1}$ by feed forward control with the use of a following formula (a):

$$BV_0\{-(\%\Delta BV_{n-1}{}'-\%\Delta BV_n{}')+(\%\Delta BV_n{}'-\%\Delta BV_{n+1})\}+ UFR_n \times T = UFR_{n+1} \times T \quad (a)$$

wherein $BV_0$ is the blood volume at the time of the initiation of hemodialysis; $\%\Delta BV_n{}'$ is a ratio of the blood volume change at the selected controlling point (n); $\%\Delta BV_{n-1}{}'$ is a ratio of the blood volume change in consideration of control delay at a previous controlling point (n−1) adjacent to said selected controlling point (n); $\%\Delta BV_{n+1}$ is a ratio of the blood volume change defined at a next controlling point (n+1) adjacent to said selected controlling point (n) by the target control line; T is the elapsed time until the selected controlling point (n); $UFR_n$ is the water removal speed at a selected controlling point (n); $UFR_{n+1}$ is a calculated water removal speed at which the actual working unit carries out the water removal from the selected controlling point (n) to the controlling point (n+1), to attain the target ratio of the blood volume change defined at a next controlling point (n+1).

3. The dialysis apparatus according to claim 2, wherein $\%\Delta BV_{n-1}{}'$ is determined by the alignment least square method.

4. The hemodialysis apparatus according to claim 2, wherein the distance between two adjoined controlling points is defined to be short so that there is no substantive difference between patients' $PRR_n$ shown by the following formula at each controlling point (b):

$$PRR_n - UFR_n = \Delta BV_n{}'/T_n \quad (b)$$

wherein $PRR_n$ shows the speed of blood plasma that is refilled from the body to a blood vessel at the selected controlling point (n), $UFR_n$ is a water removal speed at the selected controlling point (n), $\Delta BV_n{}'$ is the blood volume change at the selected controlling point (n), and $T_n$ is the elapsed time until the selected controlling point (n).

5. The hemodialysis apparatus according to claim 1, wherein the control member sets up a deviated control line restricting chronological change of the blood index value within a prescribed range beneath said target control line, and
wherein when the measured blood index value falls below the deviated control line, the control member controls the stop of water removal of the actual working member temporarily.

* * * * *